United States Patent [19]

Levine

[11] Patent Number: 6,034,622
[45] Date of Patent: Mar. 7, 2000

[54] LOCATION MONITORING VIA IMPLANTED RADIO TRANSMITTER

[75] Inventor: Robert A. Levine, 41 Rayfield Rd., Westport, Conn. 06880

[73] Assignee: Robert A. Levine, Westport, Conn.

[21] Appl. No.: 08/698,327

[22] Filed: Aug. 14, 1996

Related U.S. Application Data

[60] Provisional application No. 60/002,523, Aug. 18, 1995.

[51] Int. Cl.[7] .................................................. G01S 5/10
[52] U.S. Cl. ............................. 340/825.54; 340/825.49; 340/825.69; 340/825.06; 455/100; 342/385
[58] Field of Search ..................... 340/825.54, 825.49, 340/539, 573.1, 825.72, 825.37, 573.4, 825.36; 455/100; 342/126, 385, 450, 463, 146, 56, 147; 128/903; 607/32

[56] References Cited

U.S. PATENT DOCUMENTS

| | | | |
|---|---|---|---|
| 4,003,379 | 1/1977 | Ellinwood, Jr. | 128/260 |
| 4,146,029 | 3/1979 | Ellinwood, Jr. | 128/260 |
| 4,399,821 | 8/1983 | Bowers | 128/630 |
| 4,494,119 | 1/1985 | Wimbush | 343/457 |
| 4,494,950 | 1/1985 | Fischell | 604/66 |
| 4,519,401 | 5/1985 | Ko et al. | 128/903 X |
| 4,677,982 | 7/1987 | Llinas et al. | 128/664 |
| 4,706,689 | 11/1987 | Man | 128/903 |
| 4,764,111 | 8/1988 | Knierim | 433/5 |
| 4,801,921 | 1/1989 | Zigunfus | 340/573 |
| 4,843,377 | 6/1989 | Fuller et al. | 340/573 |
| 4,924,211 | 5/1990 | Davies | 340/825.54 X |
| 4,952,928 | 8/1990 | Carroll et al. | 340/825.54 |
| 5,027,314 | 6/1991 | Linwood et al. | 364/900 |
| 5,153,584 | 10/1992 | Engira | 340/870.18 |
| 5,218,344 | 6/1993 | Ricketts | 340/573 |
| 5,252,962 | 10/1993 | Urbas et al. | 340/870.17 |
| 5,314,450 | 5/1994 | Thompson | 607/32 |
| 5,324,315 | 6/1994 | Grevious | 128/903 X |
| 5,396,224 | 3/1995 | Dukes et al. | 340/825.49 |
| 5,396,227 | 3/1995 | Carroll et al. | 340/825.31 |
| 5,458,123 | 10/1995 | Unger | 128/903 X |
| 5,461,390 | 10/1995 | Hoshen | 340/825.49 X |
| 5,543,797 | 8/1996 | Hochstein et al. | 340/825.54 X |
| 5,553,616 | 9/1996 | Ham et al. | 706/924 X |
| 5,568,119 | 10/1996 | Schipper et al. | 340/825.37 |
| 5,596,313 | 1/1997 | Berglund et al. | 340/539 X |
| 5,621,388 | 4/1997 | Sherburne et al. | 340/539 X |
| 5,720,771 | 2/1998 | Snell | 607/60 |
| 5,752,976 | 5/1998 | Duffin et al. | 607/32 |
| 5,769,877 | 6/1998 | Barreras, Sr. | 607/61 |
| 5,791,344 | 8/1998 | Schulman et al. | 128/635 |
| 5,828,306 | 10/1998 | Curran | 340/573.4 |
| 5,836,989 | 11/1998 | Shelton | 607/27 |
| 5,870,029 | 2/1999 | Otto et al. | 340/825.36 |

OTHER PUBLICATIONS

D.J. Torrieri, "Statistical Theory of Passive Location Systems," IEEE Transactions on Aerospace and Electronic Systems, vol. AES–20, No. 2, Mar. 1984, pp. 183–198.

*Primary Examiner*—Michael Horabik
*Assistant Examiner*—William H. Wilson, Jr.
*Attorney, Agent, or Firm*—Fitzpatrick, Cella, Harper & Scinto

[57] ABSTRACT

An open-loop internal monitoring system comprising (a) a plurality of internal radio transmitters, each being implanted in a human for transmitting a plurality of signal pulses, each pulse being encoded with unique identifying information; (b) a plurality of external radio receivers each having a corresponding clock, for receiving each of the plurality of signal pulses transmitted by each of the plurality of internal radio transmitters and for generating from each received signal pulse a plurality of data including at least a time-of-arrival generated in accordance with the synchronized clock of the external radio receiver and the internal radio transmitter identifying information; and (c) a central processor for (1) estimating a location for each internal radio transmitter in accordance with the time-of-arrival, (2) storing, for each human, authorized or unauthorized areas to which the human is assigned, (3) determining an event of whether the estimated location is within the authorized area or the unauthorized area assigned to any one of the humans and stored in the central processor, and (4) notifying a monitor of the central processor upon occurrence of the event.

16 Claims, 8 Drawing Sheets

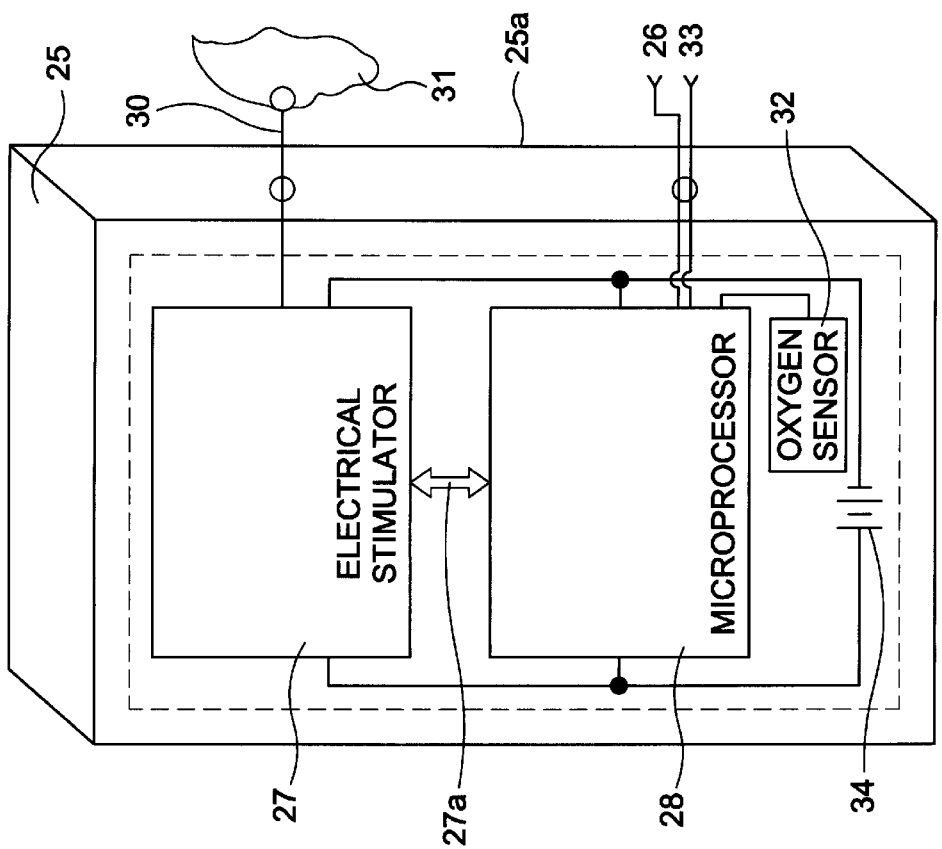
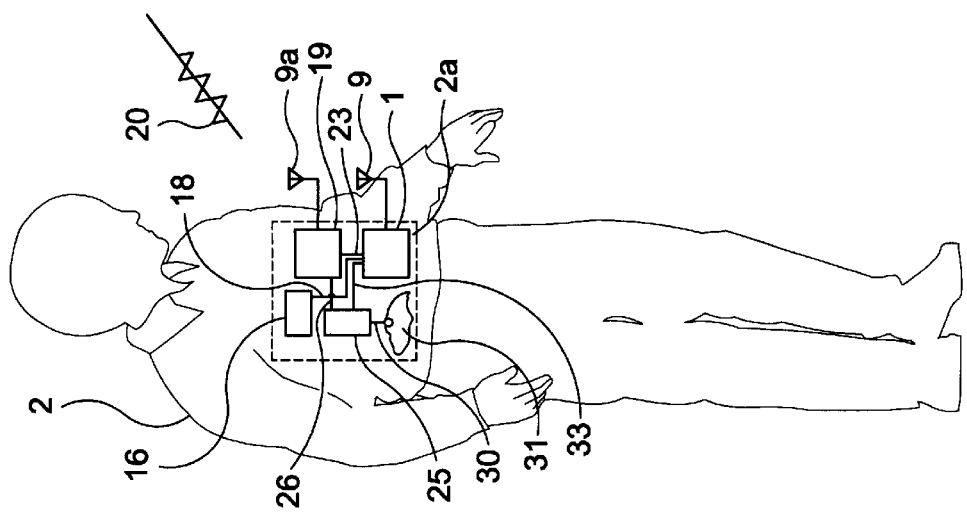

LOCATION MONITORING VIA IMPLANTED RADIO TRANSMITTER

CROSS-REFERENCE TO RELATED APPLICATIONS

This application claims the benefit of U.S. Provisional Application No. 60/002,523, filed Aug. 18, 1995.

BACKGROUND OF THE INVENTION

1. Field of the Invention

The present invention relates to a system for monitoring a location of a human by using a transmitter implanted in the human. The system may further monitor the presence of a predetermined chemical substance in the human by using an implanted substance monitoring unit. The system also controls the behavior of the human based on the monitoring by using an implanted receiver that receives a command, from a central processor such as a computer system that is analyzing the person's location or substance use, to activate an implanted behavior control unit that causes unpleasant effects in the human.

2. Description of Related Art

The overcrowding of prisons has led to the creation and use of alternative sentencing programs by the court systems. One such alternative sentence imposed is confining a prisoner in his or her home or in some other non-prison setting. This approach has led to the creation of remote monitoring systems that can determine from a centralized location whether the prisoner has left the assigned confinement area.

For example, U.S. Pat. No. 4,843,377 to Fuller et al. is directed to a remote confinement system having an external transmitter fixed at the prisoner's remote confinement area, a receiver/relaying unit and a central office computer. The central office computer identifies the prisoner and monitors the presence of a prisoner at the confinement area using information transmitted to the computer from the transmitter. The Fuller Patent also discusses other "home arrest" systems that attach bracelet radio transmitters to the prisoners. These bracelets cause an alarm to be sent to the central monitoring office via a phone transponder if the prisoner strays too far from his or her home.

One drawback of the system of the Fuller Patent and the home arrest systems disclosed therein is their fixed transmitter, which is unable to provide the monitor of the system with the prisoner's location outside the confinement area, since the transmitter merely signals his or her absence from that area. Thus, if the prisoner leaves the confinement area, his or her whereabouts will be unknown. A fixed transmitter also limits the number of confinement areas for a prisoner, as each confinement area would require installation of a transmitter. Thus, a need exists for an ambulatory transmitter that positively informs the system monitor of the location of the prisoner over a wide area so as to provide gap-free surveillance. Further, by providing coverage outside of the confinement area, an extended "confinement" area, including, for example, the prisoner's office or school, can be granted to the prisoner, which allows him or her to rehabilitate while serving his or her sentence.

Another drawback of the remote monitoring systems of the Fuller Patent is that they do not actively deter the prisoner from leaving his or her confinement area. Moreover, if the prisoner leaves the confinement area, the systems do not actively urge the prisoner to return to the confinement area, forcing the police to track down the prisoner and physically return him or her to the area. This is not only dangerous for the police and general public, but also expensive. Further, while the police are doing this, they cannot otherwise protect and serve the community. Thus, a behavior control system is needed that actively deters the prisoner from leaving the confined area, and if he or she leaves it nonetheless, urges the prisoner to return to the area.

The need for an ambulatory transmitter generally requires that the transmitter used to transmit locating signals and information regarding the prisoner's identity be externally worn by or implanted into the prisoner. Besides the above-described electronic bracelets mentioned in the Fuller Patent, externally-worn transmitters have been used to provide location signals for monitoring the locations of humans as discussed in U.S. Pat. Nos. 5,027,314 (Linwood et al.), 5,153,584 (Engira) and 5,218,344 (Ricketts). For example, the personnel monitoring system of the Ricketts Patent uses portable transmitter/receivers (transceivers), each of which is worn on the wrist of a person such as a prisoner within a correctional facility. Stationary transceivers interrogate all the portable transceivers, of which only the ones configured to respond to the interrogation signal reply. The portable transceivers respond to the stationary transceivers, which in turn demodulate and relay the response to a computer that determines the location and identity of each person.

Externally-worn transmitters such as those described in the Ricketts Patent, however, have several disadvantages when used in a monitoring system for monitoring prisoners outside a confined setting. They may be accidently or purposely damaged or altered. They may be removed by the prisoner and further, placed on a substitute for the prisoner to deceive the monitor.

Implanted transmitters, however, cannot so easily be damaged, altered or removed. But implanted transmitters have been primarily used for transmitting physiological parameters to a remote monitor, either in animals (U.S. Pat. No. 4,399,821 to Bowers) or humans (U.S. Pat. Nos. 4,677,982 to Llinas et al., 5,252,962 to Urbas et al. and 5,314,450 to Thompson), rather than transmitting signals for locating humans.

Other alternative sentences may impose certain compliance conditions on a home arrest prisoner or probationer. One such condition is ordering the prisoner to keep away from a "victim" (a protective order). A system has been created to remotely monitor compliance with a protective order (U.S. Pat. No. 5,396,227 to Carroll et al.). In the Carroll Patent, the victim keeps a sensing unit near his or her home to electronically detect the wrongful presence of the prisoner and transmit the same to a central station. Like the remote monitoring systems described above, however, the transmitting unit is stationary and thus limits the area in which the victim can safely remain.

Another condition imposed on a probationer or a home arrest prisoner is to refrain from the use of alcohol or illegal drugs. The above-described remote monitoring system of the Fuller Patent, for example, also monitors the prisoner for use of alcohol and drugs. The system includes breath alcohol and body fluid testers for determining compliance by the prisoner of the imposed substance abuse restrictions. The testers, however, are not ambulatory, and the prisoner cannot be monitored outside the fixed tester and transmitter location. This system also does not constantly test the prisoner, and thus even if the prisoner faithfully stays within the confinement area, there can be long periods of times when the prisoner's alcohol or drug use is not being monitored. Further, because the alcohol and body fluid testers are external to the prisoner, other persons can substitute their "clean" breath or fluid sample for that of the prisoner. These shortcomings allow the system to be abused. Although the system attempts to prevent this abuse by various identification measures, these methods are not foolproof and add expense and complexity to the system.

Therefore, a monitoring system having an ambulatory substance monitoring unit is needed that can monitor the use of one or more substances by the prisoner at most times and over a wide area, and does not permit substitution of another person for the prisoner or probationer. Of course, such a substance monitoring system can also be used to monitor the types and amounts of various substances present in subjects of scientific experiments without requiring the subjects to remain at a laboratory. Further, similar to the above-described need for a behavior control system for deterring a prisoner from leaving the confinement area and for urging his or her return if he or she does leave, a behavior control system is also needed for deterring a prisoner's use of unauthorized substances and for encouraging him or her to stop using the substances if he or she does use them.

A substance monitoring system generally requires the use of either an external substance monitor, with its above-described drawbacks, or an implanted monitor. Implanted monitors have been generally used for measuring physiological or biochemical parameters, for example, as described in the Bowers Patent (implanted sensors in animals for sensing blood chemistry parameters such as pH, PCO2 and PO2), the Llinas Patent (implanted sensor for measuring biochemicals) and U.S. Pat. No. 4,494,950 to Fischell (implanted glucose sensor), but not for internal monitoring of alcohol and illegal drugs.

A monitoring system may be "open-loop", that is, information flows only from the monitored person to the monitoring station. However, if behavior control based on monitoring of that person is desired, commands must be sent in a "closed-loop" manner from the monitor back to the monitored person. If this feedback is done via a radio transmitter, the commands are then received by an implanted or externally-worn radio receiver. Examples of externally-worn radio receivers are discussed in the Ricketts and Engira Patents, and implanted receivers are discussed in the Urbas, Thompson, Bowers and Llinas Patents.

Further, to control behavior, either external or internal behavior control units are required to act on command. The abdominal muscle firmness alarm of U.S. Pat. No. 4,801,921 to Zigunfus and the reminder and enforcer orthodontic apparatus of U.S. Pat. No. 4,764,111 to Knierim are two examples of external behavior control units. An implanted behavior control unit is discussed in the Fischell Patent wherein a signal is transmitted to an intracorporeal module that applies an aversive electric shock to a nerve to inhibit self-destructive behavior.

Implanted receivers, substance monitoring units and behavior control units are preferable over external devices for generally the same reasons as an implanted transmitter is preferable over an external transmitter. However, none of the above-described systems have used one or more of these implanted devices in a system that can effectively monitor or control the behavior of remotely confined prisoners or probationers.

SUMMARY OF THE INVENTION

It is an object of the present invention to provide an open-loop internal monitoring system that overcomes the above-described drawbacks of previous monitoring systems.

It is another object of the present invention to provide a closed-loop internal monitoring system that can change the transmission parameters of an implanted transmitter.

It is yet another object of the present invention to provide a closed-loop internal monitoring and behavior control system.

In accordance with one aspect of the invention, an open-loop internal monitoring system is provided that includes a plurality of internal radio transmitters, each internal radio transmitter being implanted in a human for transmitting a plurality of signal pulses, each signal pulse being encoded with at least information uniquely identifying one internal radio transmitter, a plurality of external radio receivers, each external radio receiver for receiving each of the plurality of signal pulses transmitted by each of the plurality of internal radio transmitters and for generating a plurality of received signal data, each received signal datum corresponding to each received signal pulse and including at least a time-of-arrival of the received signal pulse and the internal radio transmitter identifying information decoded from the received signal pulse, a central processor for (1) estimating a plurality of locations for each internal radio transmitter, and thus for each human, from the pluralities of received signal data generated by the plurality of external radio receivers, (2) determining an event of whether at least one of the plurality of locations is outside a predetermined area assigned to any one of the humans and stored in the central processor, and (3) notifying a monitor of the central processor upon occurrence of the event, and a plurality of relays, each relay for relaying the plurality of received signal data from each external radio receiver to the central processor.

In accordance with another aspect of the invention, an open-loop internal monitoring system is provided that includes a plurality of internal radio transmitters, each internal radio transmitter being implanted in a human for transmitting a plurality of signal pulses, each signal pulse being encoded with at least information uniquely identifying one internal radio transmitter, a plurality of substance monitoring units, each substance monitoring unit implanted in a different one of the humans and electrically connected to the implanted internal radio transmitter for detecting the presence of a predetermined amount of a predetermined substance in the one human, wherein said plurality of signal pulses are further encoded with information regarding the detection of the predetermined substance, a plurality of external radio receivers, each external radio receiver for receiving each of the plurality of signal pulses transmitted by each of the plurality of internal radio transmitters and for generating a plurality of received signal data, each received signal datum corresponding to each received signal pulse and including at least the internal radio transmitter identifying information decoded from the received signal pulse and the substance detection information, a central processor for notifying a monitor upon occurrence of the detection of the predetermined substance in any one of the humans as determined from the pluralities of received signal data from the plurality of external radio receivers, and a plurality of relays, each relay for relaying the plurality of received signal data from each external radio receiver to the central processor.

In accordance with yet another aspect of the invention, a closed-loop internal monitoring system is provided that includes a plurality of internal radio transmitters, each internal radio transmitter being implanted in a human for transmitting a plurality of signal pulses and having a plurality of transmitting parameters, each signal pulse being encoded with at least information uniquely identifying one internal radio transmitter, a plurality of external radio receivers, each external radio receiver for receiving each of the plurality of signal pulses transmitted by each of the plurality of internal radio transmitters and for generating a plurality of received signal data, each received signal datum corresponding to each received signal pulse and including at least a time-of-arrival of the received signal pulse and the internal radio transmitter identifying information decoded from the received signal pulse, a central processor for (1) estimating a plurality of locations for each internal radio transmitter, and thus for each human, from the pluralities of received signal data generated by the plurality of external radio receivers, (2) determining an event of whether at least one of the plurality of locations is outside a predetermined area assigned to any one of the humans and stored in the central processor, and (3) notifying a monitor of the central processor upon occurrence of the event, a plurality of relays, each relay for relaying the plurality of received signal data from each external radio receiver to the central processor, a plurality of internal radio receivers, each internal radio receiver implanted in a different one of the humans and electrically connected to the implanted internal radio transmitter, for receiving a command generated by the central processor, wherein the command includes information uniquely identifying one of the internal radio receivers and, upon receipt by the one internal radio receiver, causes the connected internal radio transmitter to change at least one of the plurality of transmitting parameters, an external radio transmitter for transmitting the command to the plurality of internal radio receivers, and a second relay for relaying the command from the central processor to the external radio transmitter.

In accordance with yet another aspect of the invention, a closed-loop internal monitoring and behavior control system is provided that includes a plurality of internal radio transmitters, each internal radio transmitter being implanted in a human for transmitting a plurality of signal pulses, each signal pulse being encoded with at least information uniquely identifying one internal radio transmitter, a plurality of external radio receivers, each external radio receiver for receiving each of the plurality of signal pulses transmitted by each of the plurality of internal radio transmitters and for generating a plurality of received signal data, each received signal datum corresponding to each received signal pulse and including at least a time-of-arrival of the received signal pulse and the internal radio transmitter identifying information decoded from the received signal pulse, a central processor for (1) estimating a plurality of locations for each internal radio transmitter, and thus for each human, from the pluralities of received signal data generated by the plurality of external radio receivers, (2) determining an event of whether at least one of the plurality of locations is outside a predetermined area assigned to any one of the humans and stored in said central processor, and (3) generating a command upon occurrence of the event, wherein the command includes information uniquely identifying the human for which said event occurred, a plurality of relays, each relay for relaying the plurality of received signal data from each external radio receiver to the central processor, a plurality of behavior control units, each behavior control unit implanted in a different one of the humans and electrically connected to the implanted internal radio transmitter for causing an unpleasant reaction in the human upon receipt of the command, a plurality of internal radio receivers, each internal radio receiver implanted in a different one of the humans and electrically connected to the implanted behavior control unit, for receiving the command generated by the central processor and, if the command is intended for the one human as determined by the unique human identification information, relaying the command to the connected behavior control unit, an external radio transmitter for transmitting the command to the plurality of internal radio receivers, and a second relay for relaying the command from the central processor to the external radio transmitter.

In accordance with yet another aspect of the invention, a closed-loop internal monitoring and behavior control system is provided that includes a plurality of internal radio transmitters, each internal radio transmitter being implanted in a human for transmitting a plurality of signal pulses, each signal pulse being encoded with at least information uniquely identifying one internal radio transmitter, a plurality of substance monitoring units, each substance monitoring unit implanted in a different one of the humans and electrically connected to the implanted internal radio transmitter for detecting the presence of a predetermined amount of a predetermined substance in the one human, wherein the plurality of signal pulses are further encoded with information regarding the detection of the predetermined substance, a plurality of external radio receivers, each external radio receiver for receiving each of the plurality of signal pulses transmitted by each of the plurality of internal radio transmitters and for generating a plurality of received signal data, each received signal datum corresponding to each received signal pulse and including at least the internal radio transmitter identifying information decoded from the received signal pulse and the substance detection information, a central processor for generating a command upon occurrence of the detection of the predetermined substance in the human as determined from the pluralities of received signal data from the plurality of external radio receivers, wherein the command includes information uniquely identifying the human in which the detection occurred, a plurality of relays, each relay for relaying the plurality of received signal data from each the external radio receiver to the central processor, a plurality of behavior control units, each behavior control unit implanted in a different one of the humans and electrically connected to the implanted internal radio transmitter for causing an unpleasant reaction in the one human upon receipt of the command, a plurality of internal radio receivers, each internal radio receiver implanted in a different one of the humans and electrically connected to the implanted behavior control unit, for receiving the command generated by the central processor and, if the command is intended for the one human as determined by the unique human identification information, relaying the command to the connected behavior control unit, an external radio transmitter for transmitting the command to the plurality of internal radio receivers, and a second relay for relaying the command from the central processor to the external radio transmitter.

BRIEF DESCRIPTION OF THE DRAWINGS

The various aspects of the present invention can be best understood by reference to the detailed description of the preferred embodiments set forth below taken with the drawings, in which:

FIG. 7A schematically depicts a subject of a fourth embodiment of an internal monitoring and behavior control system in accordance with the present invention.

FIG. 7B depicts a behavior control unit used in the fourth embodiment.

DETAILED DESCRIPTION OF THE PREFERRED EMBODIMENTS

Figure 1:
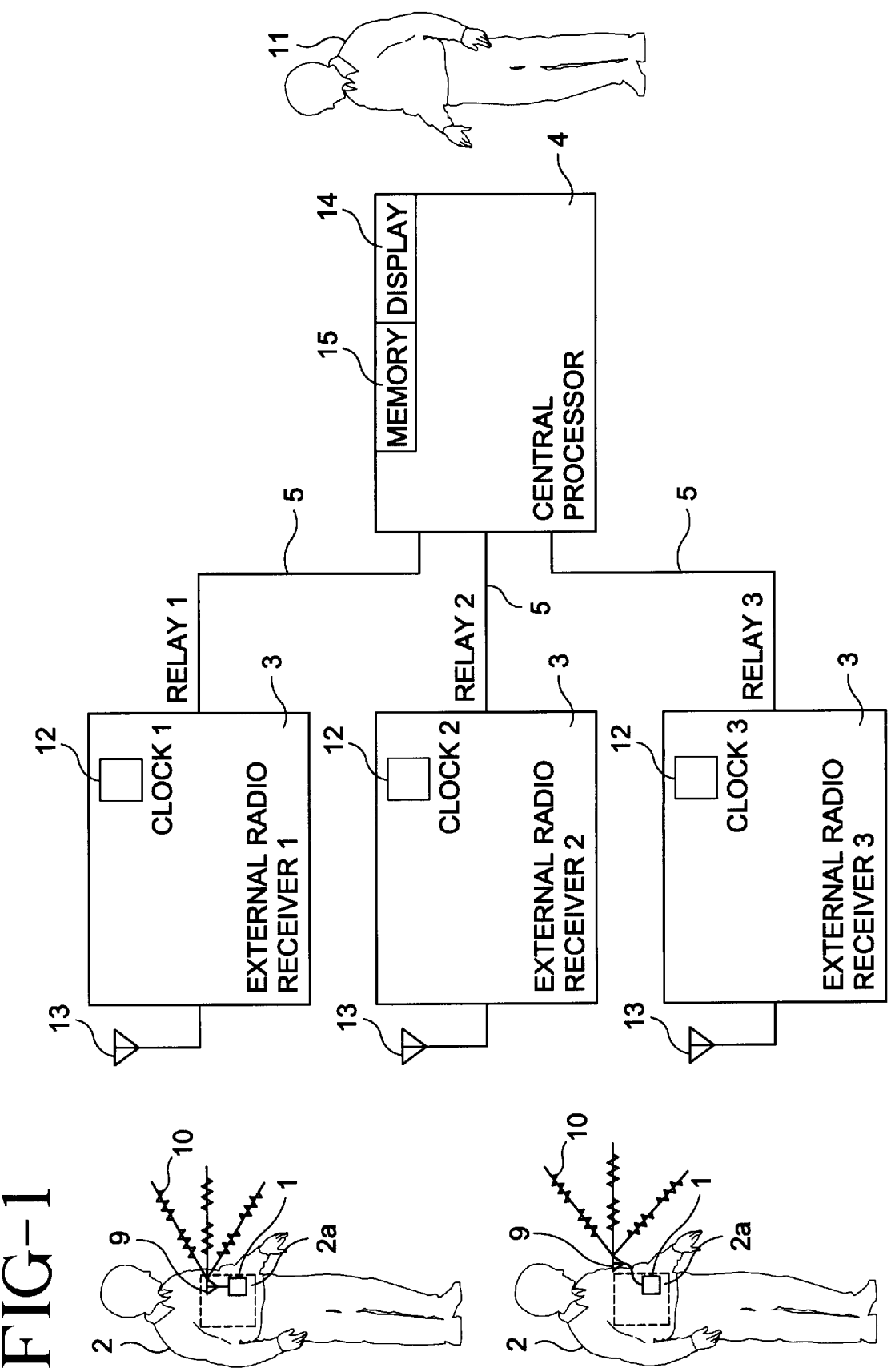
FIG. 1 schematically depicts a first embodiment of an internal monitoring system in accordance with the present invention.

FIG. 1 shows a first embodiment of the present invention in the form of an open-loop internal monitoring system for monitoring the location of one or more prisoners, probationers or experimental subjects ("subjects"). The open-loop internal monitoring system includes internal radio transmitters 1, each implanted in a different subject 2, external receivers 3 and a central processor 4. The central processor 4 is connected to the external receivers 3 by a relay 5, such as a hardwire or a standard communication link, for transmitting data.

Figure 2:
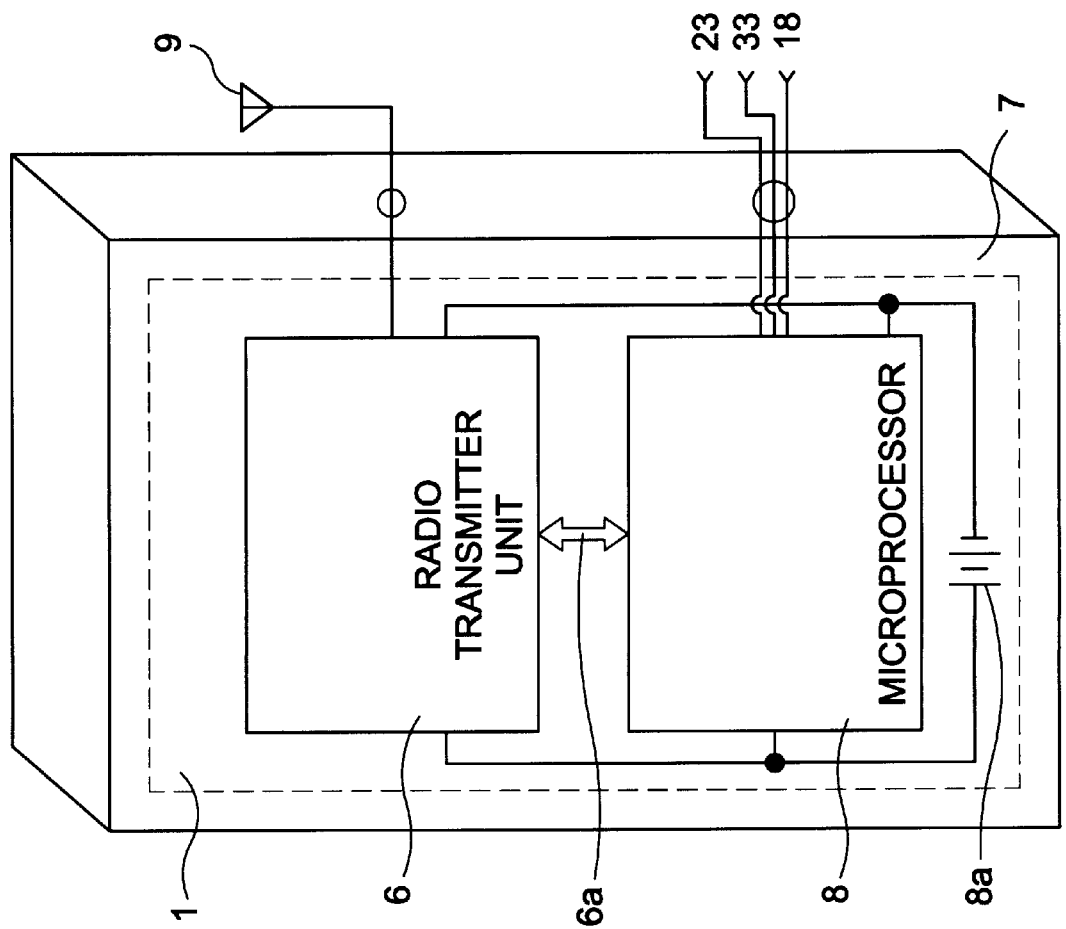
FIG. 2 depicts an internal radio transmitter.

As seen in FIG. 2, the internal radio transmitter 1 has a radio transmitter unit 6 preferably enclosed in a rigid plastic or metal, hermetically-sealed and sterile case 7. The case 7 is surgically implanted, preferably under the skin of the subject or in the subject's abdominal cavity 2a. The edges of case 7 preferably have loops and flanges (not shown) to allow it to be sutured into place, so it does not migrate within the body. A typical size for the case would be about three inches in height, four inches in width and one inch in depth, that is, approximately the size of a cardiac pacemaker.

The internal radio transmitter 1 is preferably controlled by a microprocessor 8 connected to the transmitter by bus 6a. The internal radio transmitter 1 is powered by a long-lasting battery 8a, preferably a lithium battery, with a possible 5 to 15 year lifespan based on use in a cardiac pacemaker, or by a plutonium battery, with a possible 20 to 40 year life span, also based on a cardiac pacemaker use. A transmitting antenna 9 attached to the radio transmitter unit 6 can be inside or outside the case 7. The transmitting antenna 9 may be further extended to just below the subject's skin or externally, which is preferred since this should provide more radiated power and thus greater transmission range.

Each internal radio transmitter 1 intermittently transmits radio frequency (RF) signal pulses 10 modulated with a unique code for the subject 2 in which the transmitter 1 is implanted. The unique code permits the central processor 4, and eventually a system monitor 11, to know which transmitter is the source of the signal pulses. Each signal pulse 10 has a predetermined transmission period, amplitude, duration and carrier frequency as determined by one of ordinary skill in the art to meet range, location determination and power consumption requirements, as well as any government regulations.

As shown in FIG. 1, the signal pulses 10 transmitted by one or more internal radio transmitters 1 are received by the receiving antennas 13 of external radio receivers 3 and demodulated to determine their identification code. A time-of-arrival is determined for each received signal pulse by a clock 12 within the receiver. The clocks 12 of all the external radio receivers are calibrated by standard calibration techniques well known in the art so that any time differences among them can be effectively zeroed out, thus synchronizing all the external receivers. In addition to time-of-arrival information, the external receivers 3 may use a directional antenna or antenna array in place of receiving antenna 13 to provide angle-of-arrival (bearing) information for each received signal pulse. Received signal data is generated by the external radio receivers for each received signal pulse, comprising the identification code, the time of arrival and, if applicable, the bearing of the signal pulse, as well as an identification code of the external radio receiver that received the signal pulse.

Since the transmission power of the internal radio transmitters 1 is expected to be relatively low, whether because of the need to conserve battery power in the internal radio transmitter, the use of an internal transmitting antenna or to comply with government regulations, the external radio receivers must have excellent sensitivity or be positioned close to the expected locations of the subjects. Moreover, the locations of each of the external radio receivers 3 must be accurately known by the central processor 4 for precise location determination of the subjects. This can be accomplished, for example, by traditional surveying or by using the Global Positioning System. Further, depending on which location determination algorithm is used by the central processor to compute the subject's location, at least two (if by a triangulation method) or three (if by a time-difference-of-arrival method) external radio receivers must be used for a two-dimensional location, and one more may be needed to provide a three-dimensional location. Additional external radio receivers are preferred as they will provide a wider coverage area, as well as reduce the power requirements of the internal radio transmitters. Moreover, to minimize errors in location computation due to the effects of the geometric arrangement of the external radio receivers, certain standard arrangements of the external receivers are preferable. See, for example, Torrieri, "Statistical Theory of Passive Location Systems," IEEE Transactions On Aerospace and Electronic Systems, Vol. AES-20, No. 2, March, 1984.

Further, the external radio receivers are powered by line voltage, with auxiliary generators in place to take over in case of general power failure or sabotage to the power lines. If necessary, the external radio receivers can be protected from vandalism or deliberate destruction by closed circuit television cameras capable of scanning the surrounding area and sending video back to the central processor.

The received signal data is relayed to the central processor 4 from each external radio receiver via one relay 5. The central processor is preferably a computer system with sufficient memory and speed to store and analyze the potentially large amount of received signal data from each subject. The central processor 4 collates the received signal data for each subject 2 from each external radio receiver 3 by using the signal pulse identification code. The central processor computes the locations of each subject using standard position-location algorithm based on the received signal data and the known locations of the external receivers. Each location is computed for a predetermined time. The central processor may also include a display 7 to display the location of each subject to the system monitor 11.

Each computed location and time may be stored in a memory 15 of the central processor 4, preferably in a chronological record for each subject. This chronological record of the subject's positions can be used, for example, by law enforcement personnel to determine if the subject violated a confinement or probation order, or if the subject was near a crime scene at a certain time and thus a possible suspect.

Further, a list of predetermined, authorized geographical areas for each subject is stored in the memory 15 of the central processor 4. The central processor 4 compares a location of each subject 2 to the subject's list of authorized areas and determines whether the subject is outside any of the authorized areas, i.e., is "out-of-bounds." If the subject is out of bounds, the system monitor 11 is alerted of the event. The event can also be stored in memory 15 as evidence of a violation of a confinement or probation order. Alternatively, the central processor may store a list of unauthorized areas, such as those areas in which a victim under a protective order against the subject is likely to be (for example, the victim's home or office). In this case, the system monitor 11 is notified if the subject enters an unauthorized area, and the event is stored in memory 15 as possible evidence of a violation of the protective order.

Figure 3:
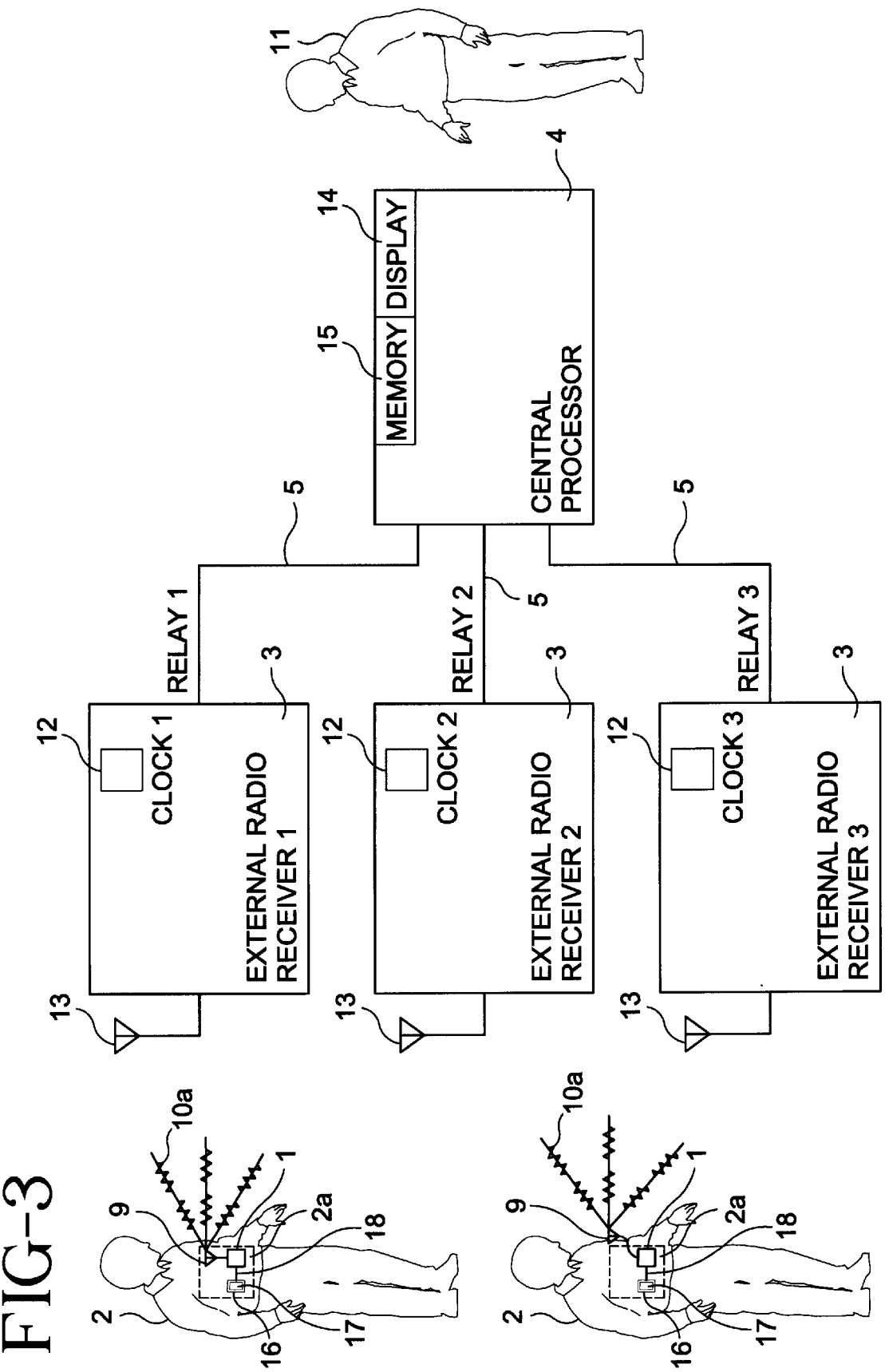
FIG. 3 schematically depicts a second embodiment of an internal monitoring system in accordance with the present invention.
Figure 4:
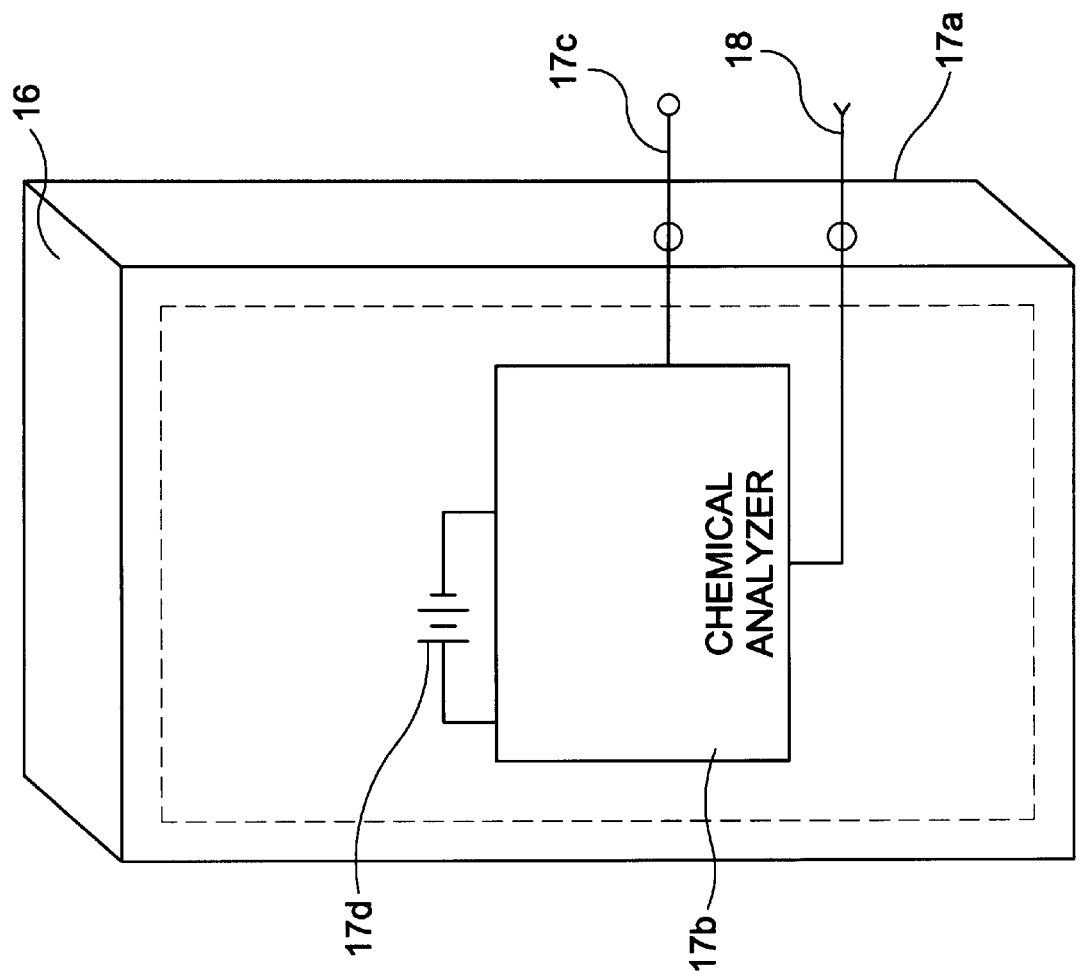
FIG. 4 depicts a substance monitoring unit.

In a second embodiment as shown in FIGS. 3 and 4, a substance monitoring unit 16 is provided in the open-loop internal monitoring system described above. The substance monitoring unit 16 further comprises a chemical analyzer 17b having a sensor 17c for assaying the presence of alcohol, a predetermined drug or other chemical substance, as shown in FIG. 4. The components of the substance monitoring unit 16 are preferably encased with the internal radio transmitter 1 and implanted therewith, sharing its power supply 8a. But the substance monitoring unit 16 and the internal radio transmitter 1 may instead be implanted separately, as shown in FIG. 3, in which case the components of the substance monitoring unit are encased in a rigid plastic or metal, hermetically-sealed and sterile case 17a and provided with its own power source, long-lasting battery 17d, preferably a lithium or plutonium battery, as shown in FIG. 4. In both cases, the sensor 17c and an input/output line 18 extend through the case. The input/output line 18 electrically connects the substance monitoring unit 16 to the internal radio transmitter 1. If the substance monitoring unit 16 is implanted apart from the internal radio transmitter 1, for example, the former in the abdominal cavity and the latter subcutaneously, the input/output line 18 that runs through the body should be shielded and sterile. A detection of one or more of the substances, and/or the raw chemical analysis data, passes over the input/output line 18 to the internal radio transmitter 1, which in turn, together with the unique identification code for the internal radio transmitter, modulates the signal pulses 10a thereof and transmits them to the external radio receivers 3.

One or more of the external radio receivers 3 receive and demodulate the signal pulses 10a. The received signal data generated by the external radio receiver 3 for each received signal pulse 10a includes at least the information from the substance monitoring unit 16 and the signal pulse's unique identification code. The received signal data may also contain the above-described location data if both substance and location system monitoring are desired. The received signal data is relayed by relay 5 to the central processor 4. The central processor 4 determines if the subject is complying with a substance-related court order by comparing the chemical detection and analysis data to a list of unauthorized substances and quantities for the subject stored a priori in the memory 15 of the central processor 4. If the subject is not in compliance, the system monitor 11 is notified, or the event is recorded in a record for the subject that is stored in memory 15 as a possible evidence of a violation of a court order.

Figure 5:
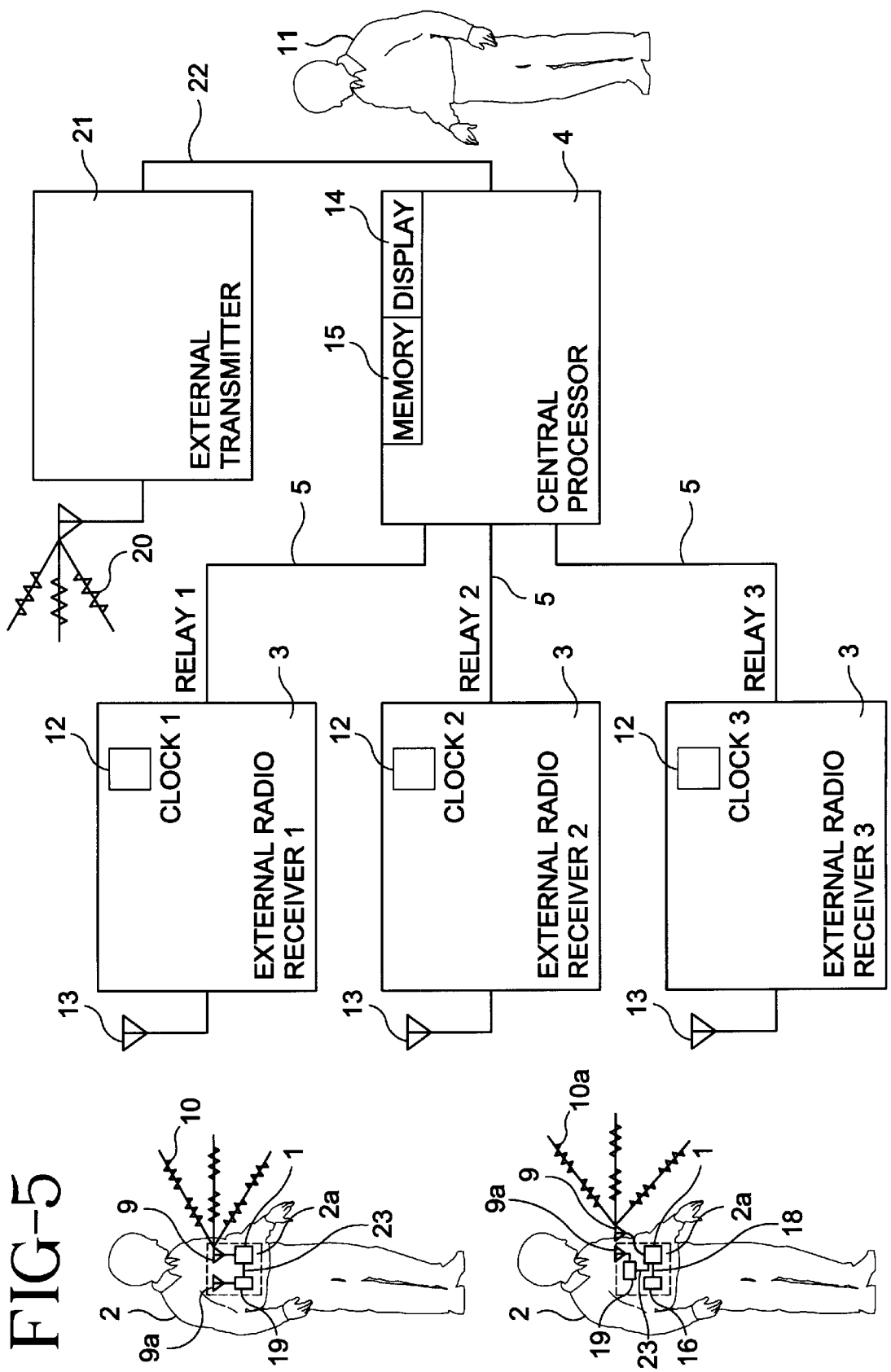
FIG. 5 schematically depicts a third embodiment of an internal monitoring system in accordance with the present invention.
Figure 6:
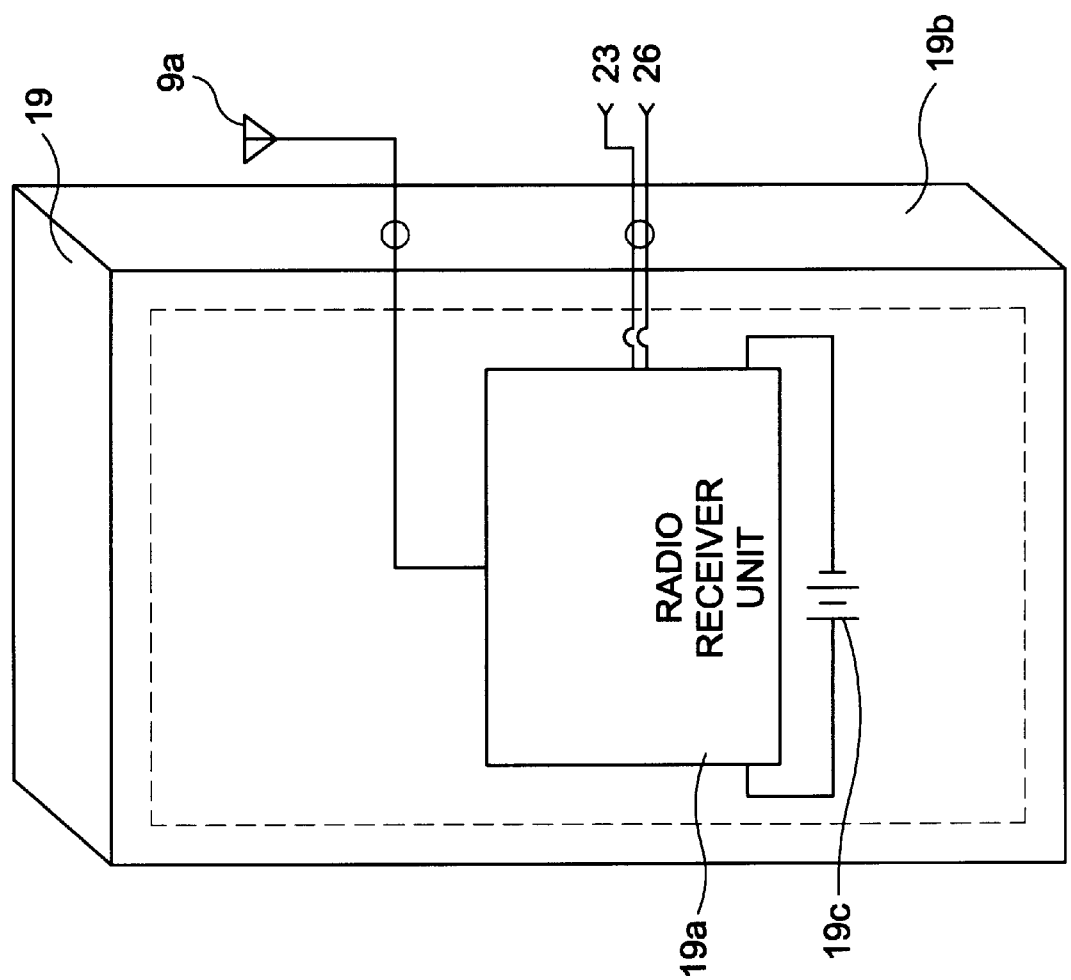
FIG. 6 depicts an internal radio receiver.

In a third embodiment, an internal radio receiver 19 is added to either of the open-loop monitoring systems of the first embodiment, as shown in the top subject 2 of FIG. 5, or the second embodiment with the substance monitoring unit 16, as shown in the bottom subject 2 of FIG. 5. The components of the internal radio receiver 19 are preferably encased with the internal radio transmitter 1, and the substance monitoring unit 16 if applicable, sharing the power supply 8a of the internal radio transmitter 1 and being implanted in the subject 2 therewith. The internal radio receiver 19 may instead be implanted separately, as shown in FIG. 5. In this case, the internal radio receiver 19 includes a radio receiving unit 19a, the receiving antenna 9a, a long-lasting battery 19c, preferably a lithium battery or a plutonium battery, which are encased in a rigid plastic or metal, hermetically-sealed and sterile case 19b, as shown in FIG. 6. In either configuration, the receiving antenna 9a may be internal or external to the case 7 or 19b, and preferably is extended to just below the subject's skin or externally for increased sensitivity. The receiving antenna 9a and transmitting antenna 9 may be the same antenna. The internal radio receiver 19 is electrically connected to the internal radio transmitter 1 by input/output line 23.

The internal radio receiver 19 is for receiving a command 20 generated by the central processor 4 as shown in FIG. 5, thus making the system closed-loop. The central processor 4 relays the command 20 via a second relay or relays 22 to one or more external radio transmitters 21 for transmission. The external radio transmitter, or array of external radio transmitters, is designed to provide wide coverage, and are powered by line voltage or by an auxiliary generators.

The command 20 has a different carrier frequency than that of the signal pulses 10 or 10a to prevent their interference. The internal radio receiver 19 receives the command 20, which in turn demodulates and decodes the command. The internal radio receiver 19 determines if the command is meant for that receiver by examining the unique receiver identification code that encoded the command. If it is, the internal radio receiver sends the command to the internal radio transmitter 1 over the input/output line 23. Otherwise, the command is ignored. The internal radio transmitter 1 changes the internal transmitter parameters as commanded as described below.

The command 20 is used to reprogram one or more of the transmitting parameters of the internal radio transmitter. For example, the period, duration or amplitude of the signal pulses 10 or 10a may be decreased to reduce power consumption, or the amplitude increased to extend transmitting range. The central processor generates the command based on the movement characteristics of the subject. For example, if the subject is not moving and it is nighttime, the subject is probably sleeping. In this situation, the command would instruct the period of the signal pulse 10 or 10a to be increased (i.e., fewer pulses are transmitted) to conserve the battery 8a of the internal radio transmitter. Conversely, if the subject was instead quickly changing his location, the command would instruct that the period be decreased to prevent losing track of the subject. The command can be also based on the received signal strength at the external radio receivers. For example, if the subject 2 is near the external radio receiver 3, the external radio receiver 3 may be receiving signal pulses 10 or 10a having a high signal to noise ratio. In this case, the command 20 would instruct the internal radio transmitter 1 to reduce the signal amplitude to conserve the battery 8a. Conversely, if the signal to noise level of the received signal pulses is low, possibly causing inaccurate location calculations, the command would instruct the internal radio transmitter to increase the signal pulse amplitude and thereby increase the received signal pulse strength and corresponding signal to noise ratio.

The fourth embodiment of the present invention is a closed-loop behavior control system shown in FIGS. 7A and 7B. The behavior control system is similar to the closed-loop system of the third embodiment, shown in FIG. 5, except that the command 20 from the central processor 4 can now direct a surgically implanted behavior control unit 25, as shown in FIG. 7A. (The command may also reprogram the internal radio transmitter as in the third embodiment.) The behavior control unit 25 is preferably encased with the internal radio transmitter 1 and internal radio receiver 19, sharing their battery 8a, and implanted in the subject 2. The substance monitoring unit 16 may also be encased and implanted therewith.

Alternatively, the behavior control unit 25 may be implanted separately from those devices, as is depicted in the subject of FIG. 7A.

As shown in FIG. 7B, the behavior control unit includes a rigid plastic or metal, hermetically-sealed and sterile case 25a, a power supply 34, preferably a long-lasting battery such as a lithium battery, and, for example, a electric stimulator 27 and a stimulating electrode 30. The electric stimulator 27 is preferably controlled by a microprocessor 28. The behavior control unit is electrically connected to the internal radio receiver 19 by receiver input/output line 26, and is further electrically connected to the internal radio transmitter 1 by transmitter input/output line 33.

One end of the stimulating electrode 30 attaches to the electrical stimulator 27. The other end extends outside the case 7 or 25a and attaches to, for example, the smooth muscle 31 of the small intestines or the autonomic nerves that innervate the small intestines. In this case, when energized by the electrical stimulator 27, the stimulating electrode adversely stimulates and contracts the muscles by applying a voltage thereto and causes mild to severe intestinal cramping, depending on the level of the voltage. Other organs or tissues, such as the smooth muscle of the large intestine, the stomach or the bladder, may alternatively be connected to the electrical stimulator 27. For this embodiment, because the behavior control unit should be near the intestines, it is preferable for it to be surgically implanted in the abdominal cavity and attached to the muscle tissue of the abdominal wall with the stimulating electrode 30 preferably passing through the peritoneal membrane to the large intestine, bladder or other organs.

The electrical stimulator 27 will activate the stimulating electrode 30 for a predetermined period of time when the command 20 from the central processor 4 is received and demodulated by the internal radio receiver 19 and is determined by the behavior control unit 25, preferably by the microprocessor 28, to be meant for the subject by examining the unique human identification code that encoded the command.

The central processor 4 will issue an activating command when its monitoring system determines the subject is out-of-bounds as described above in the first embodiment, or is using an unauthorized substance as described above in the second embodiment, and will periodically continue to reissue an activating command until the subject returns to his authorized area. The stimulator will also provide an adverse reaction each time an unauthorized substance is used, with the objective being to discourage the subject from using such substances. The stimulation voltage can be increased if the subject continues to violate the imposed restrictions, or is decreased upon compliance.

In this manner, the subject may be deterred from violating an imposed restriction under the threat of receiving an activating command. Further, if the subject violates the imposed restriction nonetheless, the subject is encouraged to meet the imposed restriction by the promise of discontinuing the activating command to stop the unpleasant effect. Moreover, the subject can be rewarded for good behavior, i.e. continued compliance, by receiving a lessened shock and milder effect, or may be punished for continued non-compliance by receiving a greater shock and stronger effect.

The behavior control unit 25 may further comprise an oxygen sensor 32. Of course, the sensor 32, can be provided with other internal components of the system. The oxygen sensor 32 is capable of detecting a predetermined amount of oxygen surrounding the behavior control unit. The oxygen sensor 32 will transmit an alarm signal to the central processor, via transmitting input/output line 33, the internal radio transmitter 1 and external radio receivers 3, if the suspect 2 removes the implanted behavior control unit 25 from his body and causes the oxygen sensor 32 to be exposed to air. The central processor 4 will then notify the monitor 11 of said oxygen detection, whereupon the appropriate law enforcement authorities can be summoned.

Figure 8:
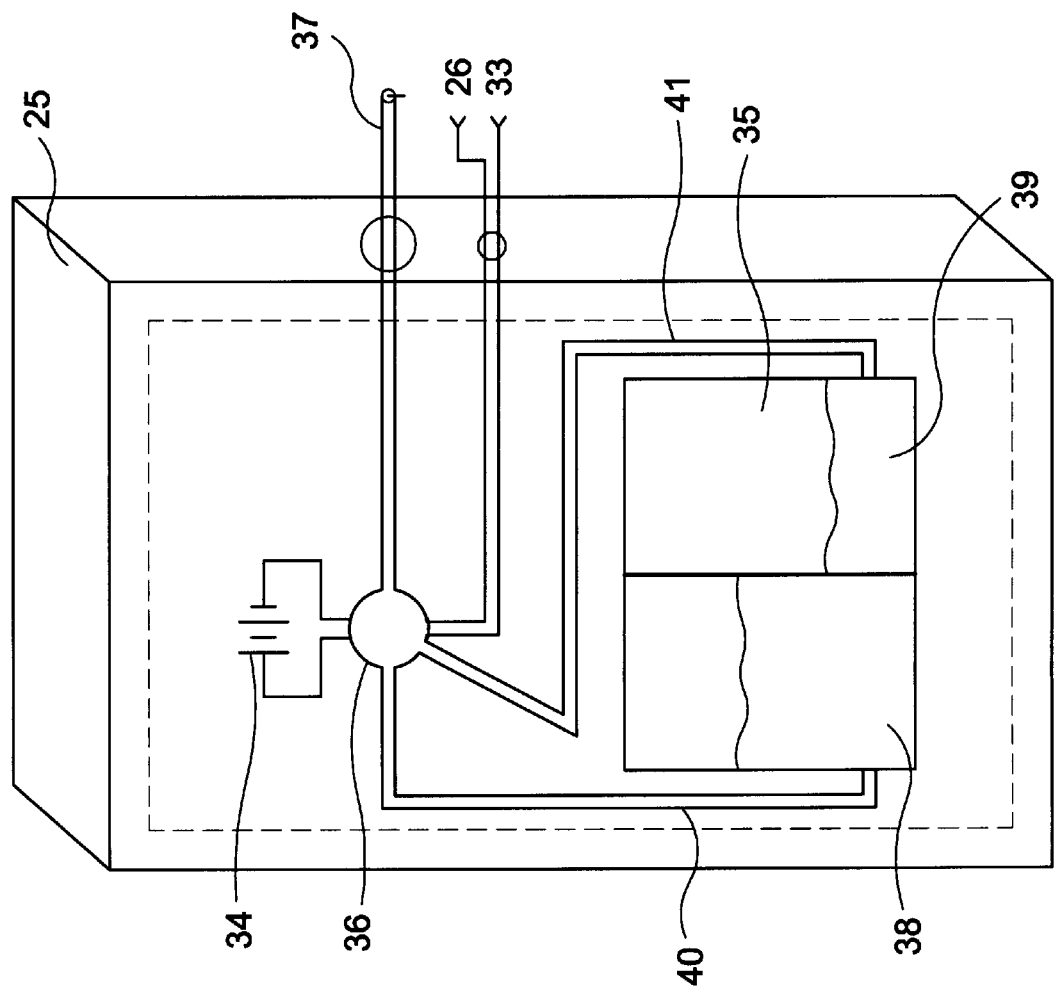
FIG. 8 depicts a behavior control unit used in a fifth embodiment of an internal monitoring and behavior control system of the present invention.

In the fifth embodiment of this invention, shown in FIG. 8, the behavior control unit uses, in place of a an electrical stimulator 27 and stimulating electrode 30, a chemical reservoir 35 and calibrated micropump 36 powered by a long-lasting battery 34. The chemical reservoir 35 is partitioned to hold a chemical 38 that can cause an adverse reaction in the subject 2, such as nausea, vomiting, cramps, dizziness, and its antidote 39. When an activating command is received by the internal radio receiver and sent to behavior control unit 25 over the receiver input/output line 26, a predetermined dose of chemical 38 is drawn from the reservoir 35 by the micropump 36 through tube 40 and is released into the blood stream or the peritoneal cavity of the subject by dispensing tube 37. Upon receiving a deactivating command, antidote 39 is instead drawn from reservoir 35 by the micropump 36 through tube 41 and is dispensed by the dispensing tube 37, thus counteracting the adverse reaction.

The amount of chemical 38 or antidote 39 dispensed can be sent back to the central processor 4, via the transmitter input/output line 33, the internal radio transmitter 1 and the external radio receivers 3. Similar to the amount of voltage applied to the stimulating electrode 30 of the fourth embodiment, the amount of chemical 38 dispensed can be increased if the subject continues to violate the imposed restriction, or can be decreased upon compliance, thus providing behavior control and modification.

From the above detailed description of the preferred embodiments, it will be appreciated that the present invention provides a system that can effectively monitor the location or substance use of remotely confined prisoners or probationers. It will be further appreciated that the present invention provides a monitoring system that uses feedback to reprogram one or more of the transmitting parameters to conserve transmitter battery power or extend transmission range. Finally, it will be appreciated that the present invention provides a system for monitoring and controlling the behavior of those prisoners or probationers.

Of course, it will be appreciated that the invention may take forms other than those specifically described, and the scope of the invention is to be determined solely by the following claims.

What is claimed is:

1. An open-loop internal monitoring system comprising:
   a plurality of internal radio transmitters, each said internal radio transmitter being implanted in a human for transmitting a plurality of signal pulses, each said signal pulse being encoded with at least information uniquely identifying one said internal radio transmitter;

a plurality of external radio receivers each having a corresponding clock, with said clocks associated with said external radio receivers being synchronized, each said external radio receiver for receiving each of said plurality of signal pulses transmitted by each of said plurality of internal radio transmitters and for generating from each said received signal pulse a plurality of data including at least (1) a time-of-arrival of when said signal pulse was received by said external radio receiver, the time-of-arrival being generated in accordance with said synchronized clock of said external radio receiver and (2) said internal radio transmitter identifying information decoded from said received signal pulse by said external radio receiver;

a central processor for (1) estimating a location for each said internal radio transmitter, and thus for each said human, in accordance with the time-of-arrival generated by each of said plurality of external radio receivers, (2) storing, for each said human, authorized or unauthorized areas to which said human is assigned, (3) determining an event of whether the estimated location is within said authorized area or said unauthorized area assigned to any one of said humans and stored in said central processor, and (4) notifying a monitor of said central processor upon occurrence of said event; and a plurality of relays, each relay for relaying said plurality of data from each said external radio receiver to said central processor.

2. An open-loop internal monitoring system according to claim 1, further comprising:

a plurality of substance monitoring units, each said substance monitoring unit implanted in a different one of said humans and electrically connected to said implanted internal radio transmitter for detecting the presence of a predetermined amount of a predetermined substance in said one human, wherein said plurality of signal pulses are further encoded with information regarding the detection of said predetermined substance, said plurality of data also includes said substance detection information received by said external radio receiver, and said central processor notifies said monitor of the detection of the predetermined substance in said human.

3. An open-loop internal monitoring system according to claim 1, wherein each said internal radio transmitter comprises:

a case, said case being hermetically-sealed and sterile;
a radio transmitter unit encased in said case; and
an antenna connected to said radio transmitter unit.

4. An open-loop internal monitoring system according to claim 3, wherein each said internal radio transmitter further comprises:

a processor electrically connected to said radio transmitter unit for controlling said radio transmitter unit.

5. An open-loop internal monitoring system according to claim 3, wherein said antenna is partially positioned below said human's skin.

6. An open-loop internal monitoring system according to claim 1, wherein said internal radio transmitter is surgically implanted below the skin of said human.

7. An open-loop internal monitoring system according to claim 1, wherein said plurality of external radio receivers comprises at least three external radio receivers and said central processor estimates location by a hyperbolic method using said times-of-arrival of said pluralities of data.

8. An open-loop internal monitoring system according to claim 1, wherein said plurality of external radio receivers comprises at least two external radio receivers, wherein each said datum generated by each said external radio receiver further includes a bearing of said received signal pulse as determined by said external radio receiver, and said central processor estimates location by a triangulation method using said bearings of said pluralities of data.

9. An open-loop internal monitoring system according to claim 1, wherein said plurality of locations for each said internal radio transmitter is stored in a memory of said central processor.

10. An open-loop internal monitoring system according to claim 1, wherein said event is stored in a memory of said central processor.

11. An internal monitoring system comprising:

a plurality of internal radio transmitters and substance monitoring units respectively electrically connected thereto, the substance monitoring units detecting the presence of a predetermined amount of a predetermined substance in said human, each said internal radio transmitter and substance monitoring unit being implanted in a respective human for transmitting a plurality of signal pulses, each said signal pulse being encoded with at least (i) information uniquely identifying one said internal radio transmitter and (ii) information regarding the detection by said substance monitoring unit of the predetermined substance;

a plurality of external radio receivers each having a corresponding clock, with said clocks associated with said external radio receivers being synchronized, each said external radio receiver for receiving each of said plurality of signal pulses transmitted by each of said plurality of internal radio transmitters and for generating from each said received signal pulse a plurality of data including at least (1) a time-of-arrival of when said signal pulse was received by said external radio receiver, the time-of-arrival being generated in accordance with said synchronized clock of said external radio receiver, (2) said internal radio transmitter identifying information decoded from said received signal pulse by said external radio receiver, and (3) information regarding the detection by said substance monitoring unit of the predetermined substance;

a central processor for (1) estimating a location for each said internal radio transmitter, and thus for each said human, in accordance with the time-of-arrival generated by each of said plurality of external radio receivers, (2) storing, for each said human, authorized or unauthorized areas to which said human is assigned, (3) determining an event of whether the estimated location is within said authorized area or said unauthorized area assigned to any one of said humans and stored in said central processor, (4) notifying a monitor of said central processor upon occurrence of said event, (5) storing, for each said human, a list of authorized or unauthorized substances and quantities thereof, (6) comparing the information regarding the detection by said substance monitoring unit of the predetermined substance with the list of authorized or unauthorized substances and quantities thereof, and (7) notifying the monitor of said central processor in accordance with the comparison; and a plurality of relays, each relay for relaying said plurality of data from each said external radio receiver to said central processor.

12. An internal monitoring system according to claim 11, wherein said substance monitoring unit detects, as the predetermined substance, alcohol.

13. An internal monitoring system according to claim 11, wherein said substance monitoring unit detects, as the predetermined substance, an illegal narcotic.

14. An internal monitoring system according to claim 11, wherein said central processor stores the estimated location and the corresponding time for each of a plurality of estimated locations so as to create a chronological record for each said human.

15. An internal monitoring system according to claim 11, wherein each said human has an internal radio receiver implanted therein for receiving signals from said central processor, the signals being generated by said central processor in accordance with (a) the determination of the event of whether the estimated location is within said authorized area or said unauthorized area assigned to any one of said humans and stored in said central processor or (b) the comparison of information regarding the detection by said substance monitoring unit of the predetermined substance with the list of authorized or unauthorized substances and quantities thereof, wherein the predetermined substance is alcohol or an illegal narcotic.

16. An internal monitoring system comprising:

a plurality of internal radio transmitters, each said internal radio transmitter being implanted in a human for transmitting a plurality of signal pulses, each said signal pulse being encoded with at least information uniquely identifying one said internal radio transmitter;

a plurality of external radio receivers each having a corresponding clock, with said clocks associated with said external radio receivers being synchronized, each said external radio receiver for receiving each of said plurality of signal pulses transmitted by each of said plurality of internal radio transmitters and for generating from each said received signal pulse a plurality of data including at least (1) a time-of-arrival of when said signal pulse was received by said external radio receiver, the time-of-arrival being generated in accordance with said synchronized clock of said external radio receiver and (2) said internal radio transmitter identifying information decoded from said received signal pulse by said external radio receiver;

a central processor for (1) estimating a location for each said internal radio transmitter, and thus for each said human, in accordance with the time-of-arrival generated by each of said plurality of external radio receivers, (2) storing, for each said human, authorized or unauthorized areas to which said human is assigned, (3) determining an event of whether the estimated location is within said authorized area or said unauthorized area assigned to any one of said humans and stored in said central processor, and (4) notifying a monitor of said central processor upon occurrence of said event; and a plurality of relays, each relay for relaying said plurality of data from each said external radio receiver to said central processor.

* * * * *

UNITED STATES PATENT AND TRADEMARK OFFICE
CERTIFICATE OF CORRECTION

PATENT NO. : 6,034,622

DATED : March 7, 2000

INVENTOR(S) : ROBERT A. LEVINE

It is certified that error appears in the above-identified patent and that said Letters Patent is hereby corrected as shown below:

COLUMN 6

Line 33, "each the" should read --each--.

COLUMN 10

Line 25, "generators." should read --generator.--.

COLUMN 11

Line 18, "a electric" should read --an electric--.

COLUMN 12

Line 7, "sensor 32," should read --sensor 32--;
   Line 31, "blood stream" should read --bloodstream--.

COLUMN 14

Line 20, "said human," should read --a human,--.

Signed and Sealed this

Seventeenth Day of April, 2001

Attest:

NICHOLAS P. GODICI

Attesting Officer     Acting Director of the United States Patent and Trademark Office